United States Patent [19]

Herron

[11] Patent Number: 4,686,364

[45] Date of Patent: Aug. 11, 1987

[54] IN SITU DETERMINATION OF TOTAL CARBON AND EVALUATION OF SOURCE ROCK THEREFROM

[75] Inventor: Susan L. Herron, Danbury, Conn.

[73] Assignee: Schlumberger Technology Corporation, New York, N.Y.

[21] Appl. No.: 756,613

[22] Filed: Jul. 19, 1985

[51] Int. Cl.$^4$ .............................................. G01V 5/00
[52] U.S. Cl. .................................. 250/256; 250/253; 250/265
[58] Field of Search ........................ 250/253, 256, 265

[56] References Cited

U.S. PATENT DOCUMENTS

| | | | |
|---|---|---|---|
| 3,321,625 | 5/1967 | Wahl | 250/71.5 |
| 3,453,433 | 7/1969 | Alger et al. | 250/83.3 |
| 3,521,064 | 7/1970 | Moran et al. | 250/83.3 |
| 3,946,226 | 3/1976 | Smith, Jr. | 250/256 |

OTHER PUBLICATIONS

"The Gamma Spectrometer Tool Inelastic and Capture Gamma-Ray Spectroscopy for Reservoir Analysis", by Westaway et al., SPE 9461, 1980.
"Carbon/Oxygen Interpretation—A Theoretical Model", by Gilchrist et al., SPWLA 24th Annual Logging Symposium, Jun. 1983.
"Neutron-Excited Gamma Ray Spectrometry for Well Logging", by Hertzhog et al., IEEE Trans. on Nuclear Science, vol. NS-26, No. 1, Feb. 1979.
"Source Rock Characterization Using Multivariate Analysis of Log Data", by Mendelson et al., SPWLA 26th Ann. Logging Symposium, Jun. 1985.
"The Continuous Carbon/Oxygen Log—Basic Concepts and Recent Field Experiences", by Hopkinson et al., J. Pet. Tech., Oct. 1982.
Autric, A. et al., "Resistivity, Radioactivity and Sonic Transit Time Logs to Evaluate the Organic Content of Low Permeability Rocks", SPWLA 26th Ann. Logging Symposium, Jun. 17–20, 1985, pp. 36–45.
Cornford, C., "Source Rocks and Hydrocarbons of the North Sea", Introduction to the Geology of the North Sea, Glennie, editor, Blackwell Scientific Publications, Oxford, England, pp. 171, 177, 1984.

(List continued on next page.)

Primary Examiner—Craig E. Church
Assistant Examiner—John C. Freeman
Attorney, Agent, or Firm—David P. Gordon; Stephen L. Borst; David G. Coker

[57] ABSTRACT

A method for determining in situ the carbon content of a source rock comprises determining the carbon/oxygen elemental ratio of the formation via inelastic gamma spectroscopy, determining the porosity of the formation, obtaining the oxygen contents and densities of the fluid and minerals in said formation, and determining the carbon content from said carbon/oxygen ratio, and said oxygen contents and densities of the fluid and minerals. The density of the fluid may be assumed, as may the oxygen content of both the formation fluid and minerals. The mineral density may also be assigned a constant value based on lithology. An alternative total carbon content determination is made by additionally determining the fractional volume, density, and oxygen content of the organic matter in the formation, and the combined mineral-organic matter density, and combining this additional information with the previously-listed determinations. The oxygen content of the organic matter may be assumed and the density of the organic matter may be assigned a constant value. The fractional volume of organic matter is calculated by using the previously determined carbon content multiplied by a weight to volume conversion factor. The combined mineral-organic matter density is determined from the densities and volumes of the organic matter and minerals. The organic matter volume may be combined with the other information to provide the alternative total carbon content determination. By eliminating the carbon contributed to the total carbon determination by formation carbonates, total organic carbon may be determined and source rocks identified and evaluated.

20 Claims, 4 Drawing Figures

OTHER PUBLICATIONS

Dellenbach, J., et al., "Source Rock Logging", *SPWLA-8th European Formation Evaluation Symposium Transactions*, Mar. 14–15, 1983, England.

Fertl, W. H. et al., "Gamma Ray Spectral Evaluation Techniques Identify Fractured Shale Reservoirs and Source-Rock Characteristics", *J. Pet. Tech.*, Nov. 1980, pp. 2053–2062.

Fertl, W. H. et al., "Gamma Ray Spectral Evaluation Techniques Identify Fractured Shale Reservoirs and Source Rock Characteristics", *SPE* 8454, 1979.

Hunt, J. M., *Petroleum Geochemistry and Geology*, W. H. Freeman and Company, San Francisco, 1979, pp. 270–271.

Meyer, B. L. et al., "Identification of Source Rocks on Wireline Logs by Density/Resistivity and Sonic Transit Time/Resistivity Crossplots", *AAPG Bulletin*, vol. 68, No. 2, (1984), pp. 121–129.

Roscoe, B. A. et al., "Response of the Carbon/Oxygen Measurement for an Inelastic Gamma Ray Spectroscopy Tool", *SPE* 14460, 1985.

*Schlumberger Log Interpretation Charts*, (1985), p. 28.

Schmoker, J. W., "Determination of Organic Matter Content of Appalachian Devonian Shales from Gamma-Ray Logs", *AAPG Bulletin*, vol. 65, (1981), pp. 1285–1298.

Schmoker, J. W., "Determination of Organic Content of Appalachian Devonian Shales from Formation-Density Logs", *AAPG Bull.*, vol. 63, No. 9, Sep. 1979, pp. 1504–1509.

Schmoker, J. W. et al., "Organic Carbon in Bakken Formation United States Portion of Williston Basin", *AAPG Bull.*, 67, No. 12, Dec. 1983, pp. 2165–2174.

Tissot, B. P. et al., *Petroleum Formation and Occurrence*, Springer-Verlag, Berlin (1978), pp. 132, 429–431.

Tixier, M. P. et al., "Oil Shale Yield Predicted from Well Logs", *7th World Petroleum Congress*, Mexico City, 1967, pp. 713–715.

IN SITU DETERMINATION OF TOTAL CARBON AND EVALUATION OF SOURCE ROCK THEREFROM

BACKGROUND OF THE INVENTION

The present invention relates to the determination, in situ, of the carbon content of source rocks of a formation. More particularly, the invention relates to methods for using the carbon/oxygen ratios produced by well logging tools to identify formation source rocks and to determine the quantity of organic matter located in the source rocks.

In the exploration for and production of hydrocarbons, it is generally valuable to analyze the geological basin involved. In determining the hydrocarbon generation potential of an area, source rocks (i.e. any rock capable of producing hydrocarbons) must be identified, along with volume (axial extent and thickness) of the rock and the quantities of organic matter contained therein. Indeed, the presence or absence of a source rock can be the determining factor in whether a drill operator drills deeper or abandons a well. Also valuable is a determination of the type of organic matter contained in the source rock as well as a determination as to whether the organic matter has matured sufficiently to produce oil or gas. Finally, it is desirable to determine whether the oil or gas has migrated out of the source rock into a reservoir.

Currently, an in situ identification of source rock is rarely undertaken due to the uncertainty of the results. Some have tried to equate a decrease in shale densities, an increase in uranium, or an increase in gamma ray activities as being proportional to the total organic carbon content of the shale. See Schmoker, J.W., "Determination of Organic Matter Content of Appalachian Devonian Shales from Gamma-Ray Logs" *AAPG Bulletin*, Vol. 65 p. 1285-1298, (1981). Others have inferred the presence of source rock from high gamma ray activity, low density, low sonic velocity, high porosity, and high resistivity. See Meyer, B.L. et al., "Identification of Source Rocks on Wireline Logs by Density/Resistivity and Sonic Transit Time/Resistivity Crossplots" *AAPG Bulletin*, Vol. 68 p. 121-129, (1984). The relationships hypothesized in the above-mentioned publications, however, appear to be of limited applicability, such as for the detection of relatively rich source rocks, and are not widely used.

Because source rock identifications have rarely been successfully accomplished in situ, source rock evaluation continues to be an expensive and time consuming undertaking. Source rock evaluation requires mud cuttings, or sidewall or core cuttings and a full lab analysis of each sample. If source rock is not identified in advance, non-source rock cuttings cannot be screened, and a full analysis of each cutting must be undertaken.

It is therefore evident that a method of rapidly identifying source rocks and categorizing them in terms of their carbon content would be valuable. It would not only provide information from which to conduct a basin evaluation including a determination of total hydrocarbon yield, but it would eliminate the need to analyze cutting and sidewall samples from noncarbonaceous formations, thereby vastly reducing the amount of laboratory analysis conducted.

SUMMARY OF INVENTION

It is therefore an object of this invention to provide a method for identifying source rocks in situ and for determining the carbon content of the source rocks.

It is a further object of this invention to provide a continuous log of total carbon in a borehole from which potential source rocks may be identified and the carbon content of the source rocks may be quantified.

It is yet another object of this invention to provide a method for deriving the carbon content of a source rock from the carbon/oxygen ratio output of known logging tools.

In accordance with the objects of the invention, a method for determining in situ the carbon content of a source rock comprises measuring the carbon/oxygen elemental ratio of the formation via inelastic gamma spectroscopy, determining the porosity of the formation, obtaining the oxygen content and density of the fluid in said formation, obtaining the oxygen content and density of the minerals in said formation, and determining the carbon content from said carbon/oxygen ratio, said oxygen content and density of the fluid, and said oxygen content and density of the minerals. If desired, the density of the fluid may be assumed, as may the oxygen content of both the formation fluid and minerals. The mineral density may also be assigned a constant value based on lithology.

If desired, an alternative total carbon content determination may be made by additionally deriving and obtaining the volume, density, and oxygen content of the organic matter in the formation and the combined mineral-organic matter density, and combining this information with the previously summarized determinations. If desired, the oxygen content of the organic matter may be assumed and the density of the organic matter may be assigned a constant value. The volume of organic matter may be calculated by determining the carbon content of the formation in accord with the method invention previously summarized, and the combined mineral-organic matter density may be determined from the densities and volumes of the minerals and organic matter in the formation. Then, the organic matter volume may be combined with the other information to provide the improved total carbon content determination.

Once the total carbon content has been determined, source rocks may be identified and evaluated by eliminating the carbon contributed to the total carbon determination by formation carbonates, thereby leaving total organic carbon. The total organic carbon content may be compared to known information on source rocks so that source rocks in the formation may be identified and evaluated.

A better understanding of the invention, and additional advantages and objects of the invention will become apparent to those skilled in the art upon reference to the detailed description and the accompanying drawings.

DETAILED DESCRIPTION OF THE PREFERRED EMBODIMENTS

Figure 1:
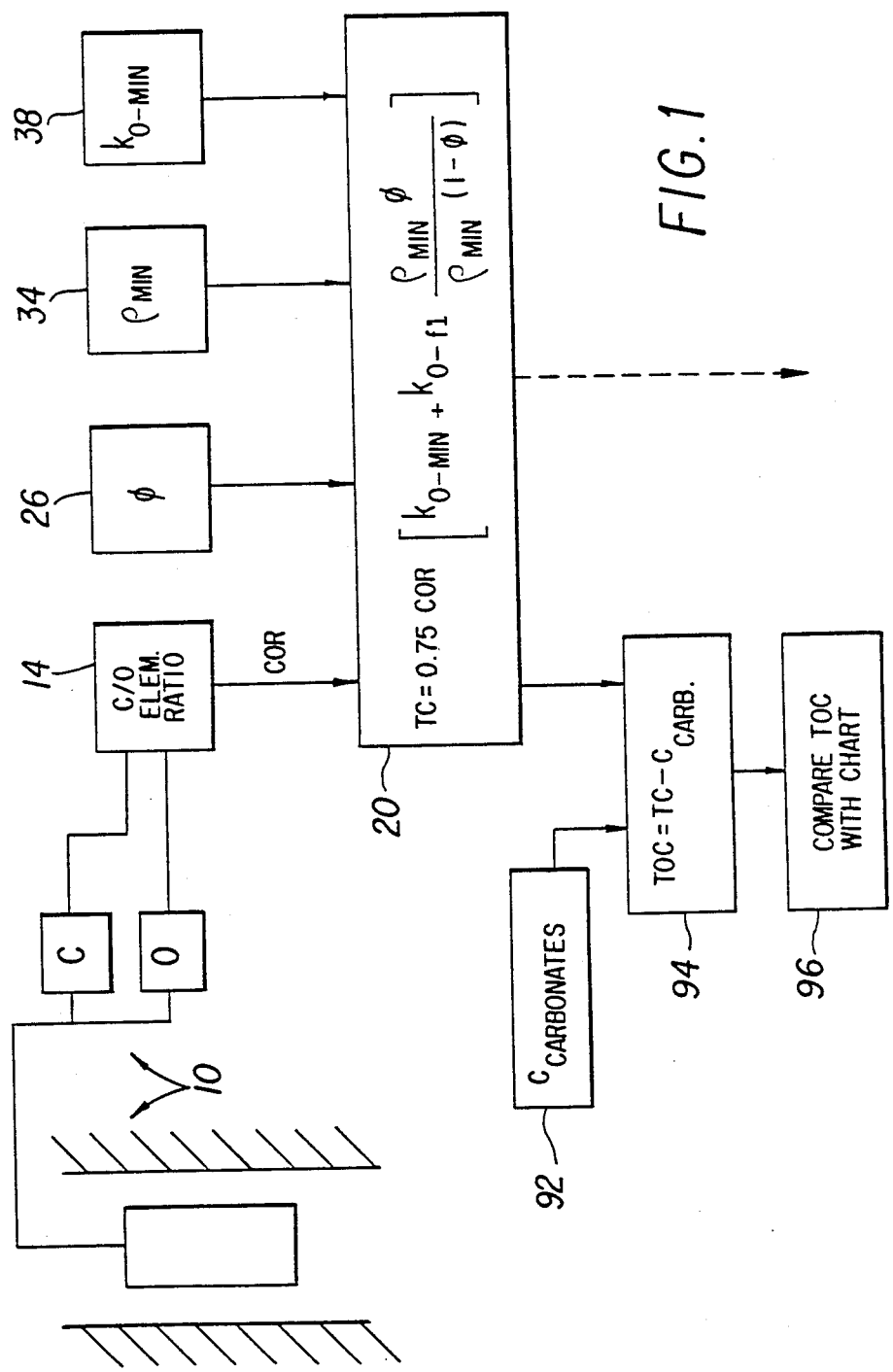
FIG. 1 is a block diagram showing the method invention according to a two component model.

A starting point in deriving the total carbon content of a formation is the use of a spectroscopy tool measuring inelastic gamma rays which can measure the carbon and oxygen yields of the formation such as is suggested by FIG. 1 at 10. Those skilled in the art will appreciate that formation logging tools, such as those disclosed in Westway, P. et al., "The Gamma Spectrometer Tool—Inelastic and Capture Gamma-Ray Spectroscopy for Reservoir Analysis", *Society of Petroleum Engineers of AIME* (SPE 9461, Sept. 21-24, 1984), will provide such yields. Typically, as disclosed in U.S. Pat. No. 3,521,064 to Moran, and in Gilchrist, W.A., et al., "Carbon/Oxygen Interpretation—A Theoretical Model: *SPWLA 24th Ann. Logging Symposium*, (June 27-30, 1983), the oxygen and carbon yields are normalized and presented as an elemental ratio at 14. The yields in the elemental ratio are both expressed in atomic concentrations (atoms/cubic centimeter of formation).

According to the invention, in deriving a total carbon content from the carbon/oxygen ratio, a two component medium may be assumed for the formation. The medium is assumed to consist of a solid matrix which contains minerals and organic matter, and a fluid-filled pore space which contains formation water. The atomic concentrations of oxygen and carbon in the formation can then be expressed as:

$$O_{form} = O_{min} + O_{fl} \quad (1a)$$

$$C_{form} = C_{min} + C_{fl} \quad (1b)$$

where the subnotations "form", "min", and "fl" are abbreviations for formation, mineral, and fluid respectively.

In a further simplification, it may be assumed that the formation minerals contain no carbon and that no hydrocarbons have migrated into or out of the formation. As a result of these assumptions, it will be seen that the entire carbon signal is attributed to organic matter in the matrix (equation (1b) being simplified thereby), while the oxygen signal is a composite of the mineral and formation water oxygen content. The mineral and formation water oxygen contents may be further obtained by:

$$O_{min} \left[ \frac{atoms\ O}{cm^3\ form} \right] = \frac{N}{16} k_{O-min} \rho_{min}(1 - \phi) \quad (2)$$

and $$O_{fl} \left[ \frac{atoms\ O}{cm^3\ form} \right] = \frac{N}{16} k_{O-fl} \rho_{min} \phi \quad (3)$$

where N is Avagadro's number, $k_O$ is oxygen concentration as a fractional weight, $\phi$ is porosity, and $\rho$ is density.

In order to derive the concentration of carbon atoms per unit volume of formation, the measured carbon/oxygen ratio must be multiplied by the oxygen concentration. Using expressions (1)-(3) above, and by converting the atomic concentration into a fractional weight, it can be shown that the total carbon in grams carbon per gram mineral is:

$$TC = 0.75\ COR \left[ k_{O-min} + k_{O-fl} \frac{\rho_{fl} \phi}{\rho_{min}(1 - \phi)} \right] \quad (4)$$

where "TC" and "COR" are abbreviations for total carbon and carbon-oxygen ratio respectively. The calculation of total carbon is made at 20 typically with the use of a computer or dedicated electronic hardware.

In order to solve relationship (4) for the total carbon in the formation, values must be provided for all of the unknowns contained therein. Thus, not only must the carbon/oxygen ratio be provided at 14 by the gamma spectroscopy tool, but the densities of the fluid and mineral, the porosity of the formation, and the oxygen concentrations as a fractional weight of the mineral and fluid are all required. Because the fluid is assumed to be water, the density of the fluid may be set equal to 1 g/cm$^3$, and the oxygen concentration as a fractional weight is 0.89 grams of oxygen per gram of water. The porosity may be determined at 26 by any of various well-known methods and may be taken from an appropriate porosity log or crossplot. Thus, the only remaining unknowns are the density of the matrix mineral, and the fractional weight of the oxygen concentration of the mineral.

Both the density and the oxygen concentration as a fractional weight of the minerals are dependent on the type of minerals found in the formation. Even without information regarding the minerals actually present, however, values for both unknowns may be assigned. Grain (mineral) density indications may be obtained at 34 in log form from a variety of tools and techniques known in the art (see, e.g. commonly owned U.S. Pat. Nos. 3,321,625 to J. S. Wahl, and 3,453,433 to R. P. Alger et al., and U.S. Ser. No. 474,481, or *Schlumberger Log Interpretation Charts* pg. 28, 1985), and may be used to solve relationship (4). Alternatively, a grain density of approximately 2.7 g/cm$^3$ may be used as a constant as there is little sensitivity in equation (4) to density variations over the density range of most of the common sedimentary minerals. Oxygen concentrations, while not obtainable without a knowledge of the minerals present, may be assigned a value, because for most of the common sedimentary minerals there is only a small variation of oxygen content. Thus, most common feldspars, clays, micas, carbonates, sulfates, etc. have an oxygen concentration of close to 50% by weight (fractional weight 0.5, or 0.085 N atoms O/cm$^3$, and a general guideline for selecting $k_{O-min}$ would be to use a value of about 0.53. Of course, if reliable mineralogy information is available such as through commonly-owned U.S. Ser. No. 474,481, more exact density and oxygen concentration values may be determined at 34 and 38 and utilized at 20.

An alternative total carbon content determination may be made by altering the assumptions regarding the composition of the formation. Instead of a two component model, the formation may be considered to consist of three components: the mineral matrix, organic matter, and fluid. Thus, relationships (1a) and (1b) are altered, and the total carbon and oxygen in the formation are expressed as:

$$C_{form} = C_{min} + C_{om} + C_{fl} \tag{5a}$$

and $$O_{form} = O_{min} + O_{om} + O_{fl} \tag{5b}$$

where subnotation "om" is an abbreviation for organic matter.

If it is assumed that the formation minerals contain no carbon, that the formation fluid is water, and that no hydrocarbons have migrated into or out of the formation, the entire carbon signal may be attributed to organic matter (equation (5a) being simplified thereby). On the other hand, the oxygen signal is now a composite of the mineral, organic matter, and formation water oxygen content. The mineral, organic matter, and formation water oxygen contents may be further obtained by:

$$O_{min} \left[ \frac{\text{atoms O}}{\text{cm}^3 \text{ form}} \right] = \frac{N}{16} k_{O-min} \rho_{min} (1 - \phi - V_{om}) \tag{6}$$

$$O_{om} \left[ \frac{\text{atoms O}}{\text{cm}^3 \text{ form}} \right] = \frac{N}{16} k_{O-om} \rho_{om} V_{om} \tag{7}$$

$$O_{fl} \left[ \frac{\text{atoms O}}{\text{cm}^3 \text{ form}} \right] = \frac{N}{16} k_{O-fl} \rho_{fl} \phi \tag{8}$$

where $V_{om}$ is the dimensionless fractional volume (volume of organic matter/volume of formation) of organic matter present in the formation.

Figure 2:
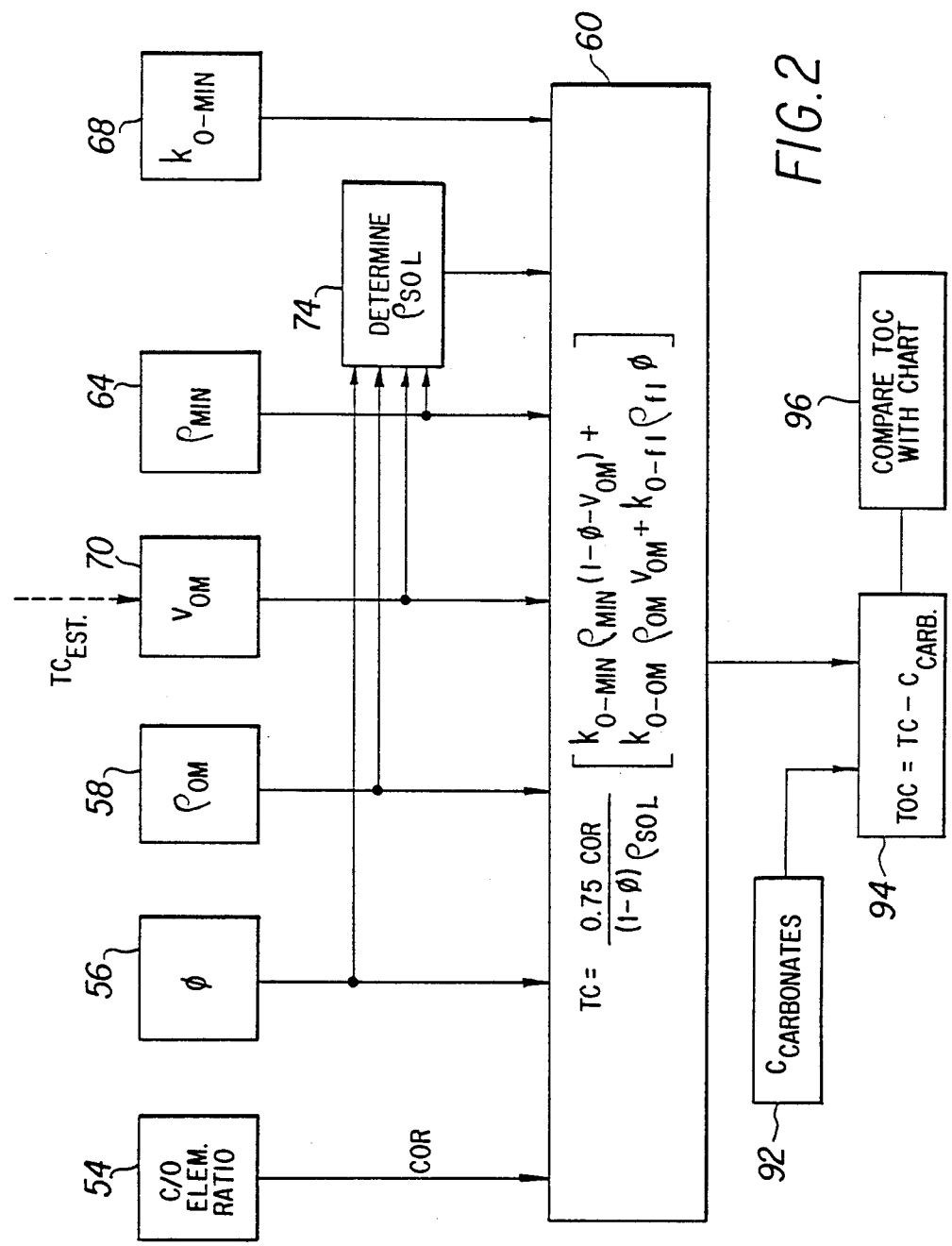
FIG. 2 is a block diagram showing an improved method according to a three component model.

Again, in order to derive the concentration of carbon atoms per unit volume of formation, the measured carbon/oxygen ratio must be multiplied by the oxygen concentration. Using expressions (5)–(8) above, and by converting the atomic concentration into weight a fractional, it can be shown that the total carbon in grams carbon per gram solid, where grams solid equals grams mineral plus is:

$$TC = \frac{0.75 \, COR}{(1 - \phi)\rho_{sol}} \left[ \begin{array}{c} k_{O-min}\rho_{min}(1 - \phi - V_{om}) + \\ k_{O-om}\rho_{om}V_{om} + k_{O-fl}\rho_{fl}\phi \end{array} \right] \tag{9}$$

where "sol" is an abbreviation for solid, and $\rho_{solid}$ is the bulk density of the combination of the minerals and organic materials in the formation. It should be noted that the term TC in equation (9) is conceptually equivalent to the TC as previously set forth in equation (4). However, because the TC of equation (9) is for the three component model, the units are different than the units of the two component model TC of equation (4);

In order to solve relationship (9) for the total carbon in the formation, values must be provided for all of the unknowns contained therein. As seen in FIG. 2, the carbon/oxygen ratio is provided at 54 through the use of normalized data gained by a gamma spectroscopy tool. The porosity is determined at 56 through the use of any of various well-known borehole tools and techniques. The density and oxygen content of the fluid, which is assumed to be water, are set at 1 g/cm³ and 0.89 grams oxygen per gram water respectively. The density of the organic matter may also be set to 1 g/cm³, as most kerogens have such a density within close approximation. If other information regarding the density of the organic matter is available, such as by Tissot, B. P. and Welte, D. H. *Petroleum Formation and Occurrence*, Springer-Verlag; Berlin (1978), the density of the organic matter may be provided at 58.

In order to determine the total carbon in the formation at 60, values must be provided for the remaining unknowns which include the density of the matrix mineral, the oxygen concentrations as fractional weights of both the mineral and the organic matter, the fractional volume of organic matter, and the density of the combination of minerals and organic matter. As hereinbefore discussed, both the density and weight percent oxygen concentration as a fractional weight of the minerals are dependent on the type of minerals found in the formation. Grain (mineral) density indications may be obtained at 64 in log form from a variety of tools and techniques known in the art, and may be used as an input into the determination of carbon content at 60. Alternatively, a grain density of approximately 2.7 g/cm³ may be used as a constant (except where there is evidence of coal, and a density of 1.5 g/cm³ should be temporarily substituted) as there is little sensitivity for density variations over the density range of most of the common sedimentary minerals. Oxygen concentrations, while not obtainable without a knowledge of the minerals present, may be assigned a value, because for most of the common sedimentary minerals there is only a small variation of oxygen content. Thus, as discussed above, a general guideline for selecting $k_{O-min}$ would be to use a value of about 0.53. Of course, if reliable mineralogy information is available such as through commonly-owned U.S. Ser. No. 474,481, more exact density and oxygen concentration values may be determined at 64 and 68 and utilized at 60.

The oxygen content of the organic matter tends to vary depending on the type of kerogen found and the maturity of the formation. As is known in the art, oxygen weight concentrations can range from nearly twenty percent (fractional weight=0.2) in immature Type III kerogens to only a couple percent in mature kerogens of any type. If geologic conditions are well known such that the appropriate kerogen type and maturity are available, a corresponding oxygen concentration may be obtained via a look-up chart. If geologic conditions are unknown, an average oxygen concentration of six percent (fractional weight=0.06) by weight may be assumed.

The final unknowns required by the three component model for the determination at 60 are the fractional volume of organic matter contained in the formation, and the density of the combination of minerals and organic matter (the latter unknown requiring knowledge of the former). These final unknowns are somewhat problematical because if the fractional volume of organic matter in the formation were known, the total carbon in the formation would be calculable directly therefrom. One approach to determining the fractional volume of organic matter is through the use of density logs according to the teachings of Meyer, B.L., and Nederlof, M.H., "Identification of Source Rocks on Wireline Logs by Density/Resistivity and Sonic Transit Time/Resistivity Crossplots, *The American Assoc. of Pet. Geologists Bulletin V.* 68, No. 2, (Feb. 1984 pp. 121-129). However, because it is believed that the fractional volume of organic matter in the formation is not accurately determinable via such techniques, an iterative procedure using the two component model is suggested and preferred. Thus, the procedure suggested by FIG. 1 and described above, which utilizes a two component model for the formation, is used to provide a preliminary determination of the total carbon in the formation. From the preliminary determination of the total carbon, a fractional weight of organic matter may be determined via a conversion factor at 70 according to the teachings of e.g. Tissot, B.P., and Welte, D.H., *Petroleum Formation and Occurrence,* Springer-Verlag, Berlin 1978 (pp. 429-431). From the fractional weight of organic matter, the volume of organic matter may be estimated from a knowledge of the bulk density of the formation, the organic matter density, and the volume of solid $(1-\phi)$ in the formation. Then, a determination may be made at 74 as to the combined density of the minerals and organic matter according to the relationship $$\rho_{solid} = \frac{(\rho_{min})(1 - \phi - V_{om})}{(1 - \phi)} + \frac{(\rho_{om})(V_{om})}{(1 - \phi)} \quad (10)$$

The fractional volume of organic matter, and the combined density may then be used as inputs for the determination at 60 of the final determination of the total carbon in the formation.

The invention using the two component model was used to calculate the total carbon in a Venezuelan formation traversed by a borehole. The carbon/oxygen ratio was provided by logging the borehole with a pulsed neutron logging tool which sensed the inelastic gamma ray spectrum resulting from the interaction of the neutrons with the formation, and by processing the information so obtained according to teachings of U.S. Pat. No. 3,521,064 to Moran, and an article by Hertzog, R.C., and Plasek, R.E., "Neutron Excited Gamma Ray Spectrometry for Well Logging", *IEEE Trans. of Nucl. Sci.* Vol. NS-26 No. 1 (Feb. 1979). Porosity was determined from a density porosity log as taught by commonly owned U.S. Pat. Nos. 3,321,625 and 3,453,433 to J.S. Wahl, and R.P. Alger et al. respectively. The grain (mineral) density was calculated from log-derived mineralogy as suggested by U.S. Ser. No. 474,481, while the mineral oxygen content was given a constant value of 0.53 grams oxygen per gram mineral. The fluid density was set to 1 g/cm$^3$, and the fluid oxygen content was set to 0.89 grams oxygen per gram of fluid. The total carbon determination was made according to relationship (4) above, and the output was provided in log format as seen by curve 80 in FIG. 3.

Figure 3:
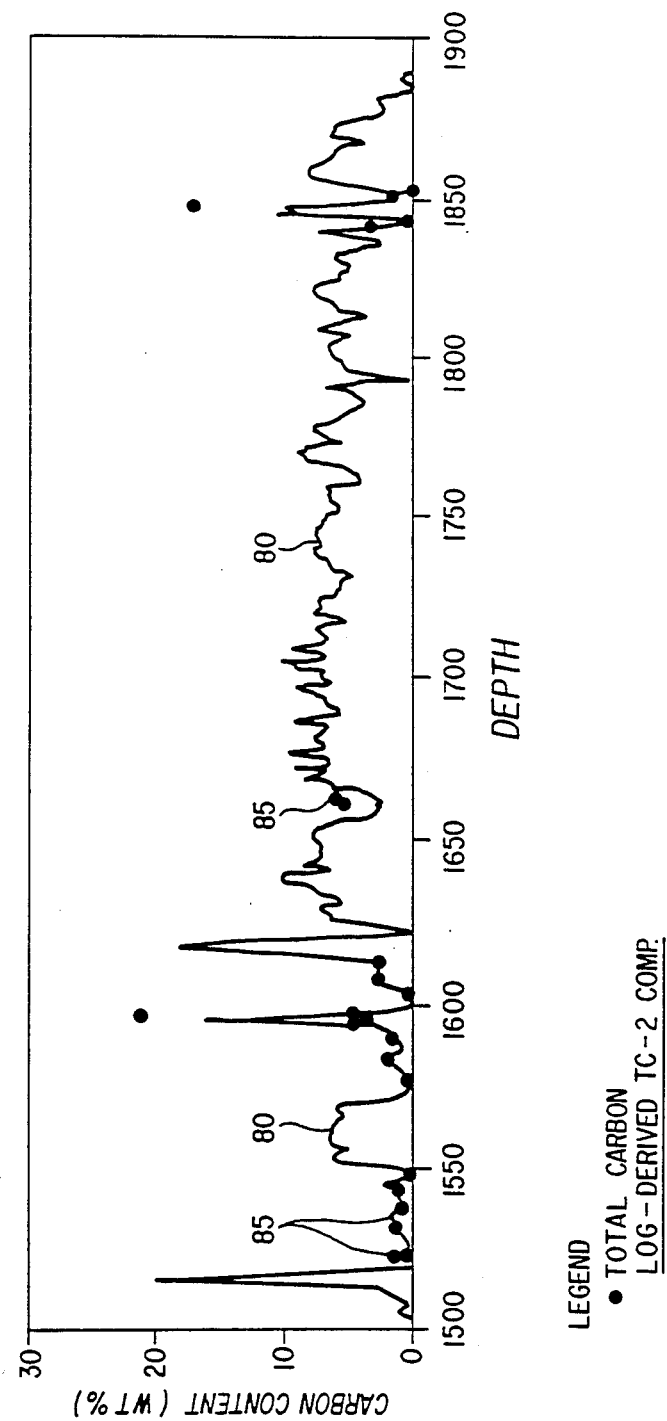
FIG. 3 is a graph comparing the in situ determination of total carbon according to the two component model invention versus the laboratory determined total carbon over depth in a borehole.

In order to prove the accuracy of the invention with regard to the total carbon determinations made in situ, over twenty sidewall samples were taken over an interval of 325 feet in both shale and coal beds. The samples were laboratory tested for total carbon content, and the results were plotted as dots 85 in FIG. 3. As seen in FIG. 3 where total carbon is plotted as a weight percentage over depth, the log-derived total carbon determination of the invention is in close agreement with the laboratory derived total carbon. This is true for relatively low carbon shales such as seen at depths 1525-1550 where carbon content is less than two percent by weight, as well as for carbon values in and adjacent to coal seams such as between depths 1844 and 1854 where the carbon content measured in excess of fifteen percent by weight.

Figure 4:
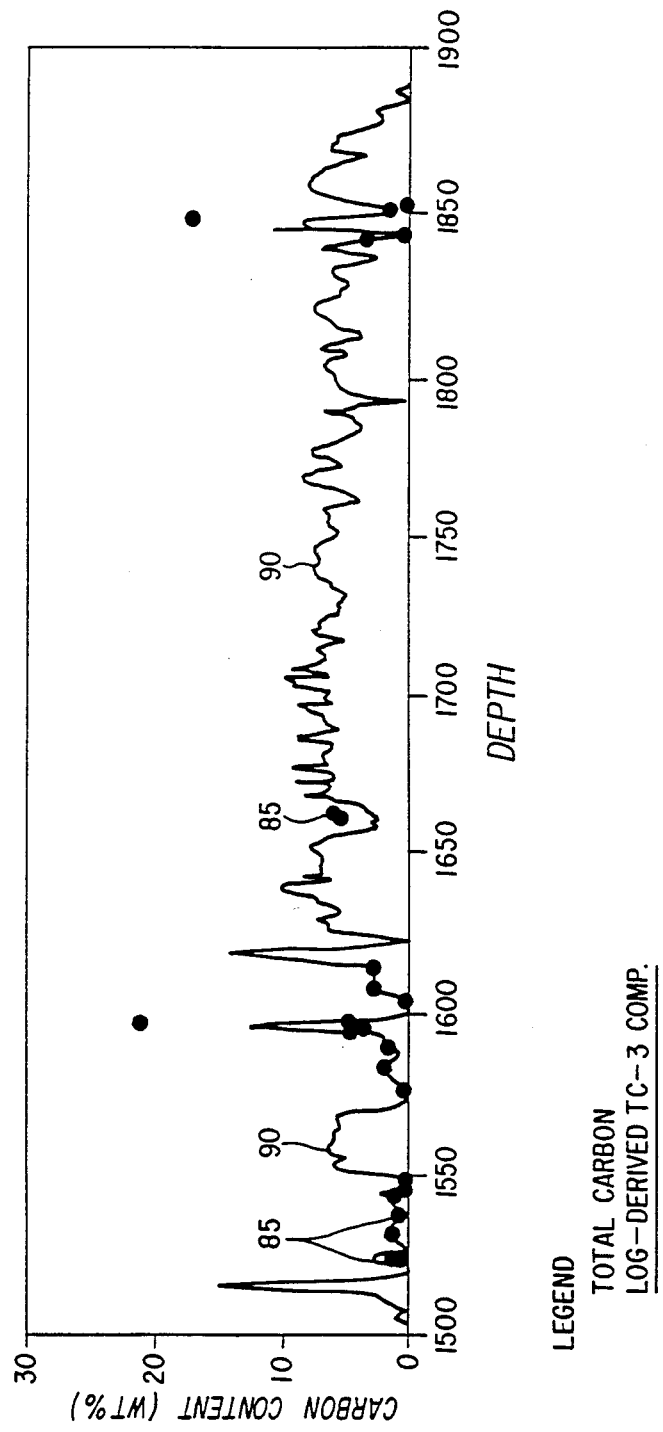
FIG. 4 is a graph comparing the in situ determination of total carbon according to the three component model invention versus the laboratory determined total carbon over depth in a borehole.

With the total carbon determination of the two component model having been accomplished, an in situ determination of total carbon was obtained via the three component model. The values obtained for the two component model for the carbon/oxygen ratio, porosity, density and oxygen content of the fluid, and density and oxygen concentration of the formation minerals were utilized. The density and oxygen content of the organic matter as a fractional weight were set as 1 g/cm$^3$ and 0.06 respectively. The fractional weight of organic matter was determined by taking the total carbon determinations of the two component model and multiplying them by a conversion factor of approximately 1.25, in accord with the teachings of Tissot and Welte as disclosed above for the type of kerogen found. Finally, after the fractional volume of organic matter was estimated by multiplying the fractional weight of the organic matter by the bulk density and the fractional volume of solid, and dividing by the density of the organic matter, the density of the mineral-organic matter combination ($\rho_{solid}$) was determined according to relationship (10) above. For each borehole depth, the obtained values were input into relationship (9), and the total carbon content was obtained and plotted as a log which is seen as curve 90 of FIG. 4. Again, the total carbon as determined by laboratory procedures on sidewall core samples are plotted as dots 85 for comparison purposes. As seen in FIG. 4, the total carbon determination made be the in situ method invention closely corresponds to the laboratory determinations.

Once a determination of the total carbon in the formation is made, it is essentially a two-step procedure to determine whether a source rock is present, and if so, to evaluate the source rock. First, it must be recognized that the total carbon determined according to the invention may be reflecting carbon in the formation rock (i.e. carbonates such as calcite, dolomite, siderite, ankerite, etc.) as well as the organic matter contained in the formation. Thus, as seen in FIGS. 1 and 2, in order to determine the amount of organic carbon in the formation, the carbon contribution of mineral carbonates ($C_{carbonates}$) determined at 92 must be subtracted at 94 from the total carbon determination. Lithology determining techniques and/or log-derived mineralogy can be used at 92 to determine the magnitude of the mineral contribution to the total carbon determination. The remaining carbon is classified as organic carbon, and its magnitude (TOC) helps determine the presence of a source rock.

The second step 96 in identifying and evaluating a source rock is comparing the determined organic carbon content with well established information in the art (which may be stored in a look-up chart). Typically, any formation containing a weight percentage of at least 0.5% organic carbon content (fractional weight of 0.005) is considered a potential source rock. In terms of quantity, weight percentages of 0.5%-1.0% are considered poor source rocks, while percentages of 1.0%-2.0% are considered fair and 2.0%-4.0% are considered good source rocks.

With the teachings of the invention as described above, it is now possible to determine in situ the carbon content of a formation, and to determine therefrom whether a source rock is present. Because a complete evaluation of source rock requires sidewall or core cuttings and a full lab analysis of each cutting, the in situ determination of the invention permits an advance screening of non-source rock cuttings. This advance screening is accompanied by large savings of time and cost. Additionally, the determination of carbon content also provides information from which to conduct a basin evaluation including a determination of total hydrocarbon yield.

There has been described and illustrated herein methods in accordance with the present invention for determining in situ the carbon content of a formation and for determining therefrom the existence and qualities of source rocks in the formation. While particular embodiments of the invention have been described, it is not intended that the invention be limited exactly thereto, as it is intended that the invention be as broad in scope as the art will permit. Thus, those skilled in the art will recognize that while the invention was described as utilizing the carbon/oxygen ratio from a tool measuring the inelastic gamma ray spectrum, any tool providing such a ratio will suffice. Likewise, while the disclosure of the invention suggested that values for certain variables be assigned a constant value or assumed, while values for other variables be determined by logging tools over depth, those skilled in the art will recognize that which variables get assigned a value, and which variables are more precisely determined might vary depending on the logging tools available, as well as prior information regarding the borehole and the geological formation. Of course, the more accurate the determination of the variables, the more accurate will be the total carbon determination at any given depth of the borehole. Moreover, while the invention was described as providing an in situ determination of total carbon, it should be recognized that computer hardware is not necessarily located downwhole, and that the determination is "in situ" in that mud, core or sidewall cuttings need not be made.

Finally, it should be understood that while the organic matter volume and the mineral-organic matter combination density of the three-component model of the invention were described as requiring an estimation of the total carbon content derived from the two-component model of the invention, these variables may be determined from any reasonable total carbon content estimate available. For the three-component model invention to be carried out, it is not required that the two-component model invention have been used. Therefore, it will be apparent to those skilled in the art that other changes and modifications may be made to the invention as described in the specification without departing from the spirit and scope of the invention as so claimed.

I claim:

1. A method for determining in situ the carbon content of a formation traversed by a borehole, comprising:
   (a) measuring the carbon/oxygen elemental ratio of said formation;
   (b) determining the porosity of the formation;
   (c) obtaining the oxygen content and density of the fluid in said formation;
   (d) obtaining the oxygen content and density of the minerals in said formation;
   (e) determining the total carbon content of said formation from said carbon/oxygen ratio, said oxygen content and density of the fluid in said formation, and said oxygen content and density of the minerals in said formation.

2. A method according to claim 1, wherein: said carbon content is determined in said determining step according to the relationship $$TC = 0.75 \, COR \left[ k_{O-min} + k_{O-fl} \frac{\rho_{fl} \phi}{\rho_{min}(1 - \phi)} \right]$$

where
TC is the total carbon in the formation;
COR is said carbon/oxygen elemental ratio;
$k_{O-min}$ is said oxygen concentration in as a fractional weight of the minerals in said formation;
$k_{O-fl}$ is said oxygen concentration as a fractional weight of the fluids in said formation;
$\phi$ is said porosity of said formation;
$\rho_{fl}$ is said density of the fluid of said formation; and
$\rho_{min}$ is said density of the minerals of said formation.

3. A method according to claim 2, wherein:
said carbon/oxygen ratio is measured by a borehole spectroscopy tool sensitive to the inelastic gamma ray spectrum.

4. A method according to claim 1, wherein:
said total carbon content is determined for a plurality of depths along said borehole in said formation.

5. A method according to claim 1, further comprising:
   (f) determining the carbon content of said minerals in said formation; and
   (g) determining the organic carbon content of said formation by subtracting said mineral carbon content from said total carbon content.

6. A method according to claim 5, wherein:
said organic carbon content is determined for a plurality of depths along said borehole in said formation.

7. A method according to claim 5, further comprising:
   (h) identifying source rocks from said organic carbon content.

8. A method according to claim 2, wherein said determined total carbon content is an estimate of total carbon content, further comprising:
   (f) obtaining the oxygen content of the organic matter in said formation;
   (g) obtaining the density of the organic matter in said formation;
   (h) deriving the fractional volume of said organic matter in said formation from said total carbon content estimate;
   (i) deriving the combined density of the organic matter and minerals in said formation from said organic matter fractional volume, said organic matter density, said porosity, and said mineral density; and
   (j) determining the total carbon content of said formation from said carbon/oxygen ratio, said porosity, said combined density of the organic matter and minerals, said oxygen content of said minerals in said formation, said oxygen content of said fluid in said formation, said oxygen content of said organic matter in said formation, said density of said minerals in said formation, said density of said fluid in said formation, said density of said organic matter in said formation, and said fractional volume of organic matter in said formation.

9. A method according to claim 8, wherein: said total carbon content is determined in said step (j) according to the relationship $$TC = \frac{0.75\ COR}{(1-\phi)\rho_{sol}} \left[ \begin{array}{l} k_{O-min}\rho_{min}(1-\phi-V_{om}) + \\ k_{O-om}\rho_{om}V_{om} + k_{O-fl}\rho_{fl}\phi \end{array} \right]$$

where
TC is the total carbon in the formation;
COR is said carbon/oxygen elemental ratio;
$k_{O\text{-}min}$ is said oxygen concentration as a fractional weight of the minerals in said formation;
$k_{O\text{-}fl}$ is said oxygen concentration as a fractional weight of the fluids in said formation;
$k_{O\text{-}om}$ is said oxygen concentration as a fractional weight of the organic matter in said formation;
$\phi$ is said porosity of said formation;
$\rho_{fl}$ is said density of the fluid of said formation;
$\rho_{min}$ is said density of the minerals of said formation;
$\rho_{om}$ is said density of the organic matter of said formation;
$V_{om}$ is said fractional volume of organic matter in said formation; and
$\rho_{sol}$ is said combined density of said organic matter and said minerals of said formation.

10. A method according to claim 8, wherein:
said total carbon content determined at step (j) is determined for a plurality of depths along said borehole in said formation.

11. A method according to claim 8, further comprising:
(k) determining the carbon content of said minerals in said formation; and
(l) determining the organic carbon content of said formation by subtracting said mineral carbon content from said total carbon content determined at step (j).

12. A method according to claim 11, wherein:
said organic carbon content is determined for a plurality of depths along said borehole in said formation.

13. A method according to claim 11, further comprising:
(m) identifying source rocks from said organic carbon content.

14. A method for determining in situ the carbon content of a formation traversed by a borehole, comprising:
(a) measuring the carbon/oxygen elemental ratio of said formation;
(b) determining the porosity of the formation;
(c) obtaining the oxygen content and density of the fluid in said formation;
(d) obtaining the oxygen content and density of the minerals in said formation;
(e) obtaining the oxygen content and density of the organic matter in said formation;
(f) obtaining an estimation of the fractional volume of organic matter in said formation;
(g) deriving the combined density of the organic matter and minerals in said formation from said organic matter fractional volume, said organic matter density, said porosity, and said mineral density; and
(h) determining the total carbon content of said formation from said carbon/oxygen ratio, said porosity, said combined density of the organic matter and minerals, said oxygen content of said minerals in said formation, said oxygen content of said fluid in said formation, said oxygen content of said organic matter in said formation, said density of said minerals in said formation, said density of said fluid in said formation, said density of said organic matter in said formation, and said estimate of fractional volume of organic matter in said formation.

15. A method according to claim 14, wherein: said total carbon content is determined according to the relationship $$TC = \frac{0.75\ COR}{(1-\phi)\rho_{sol}} \left[ \begin{array}{l} k_{O-min}\rho_{min}(1-\phi-V_{om}) + \\ k_{O-om}\rho_{om}V_{om} + k_{O-fl}\rho_{fl}\phi \end{array} \right]$$

where
TC is the total carbon in the formation;
COR is said carbon/oxygen elemental ratio;
$k_{O\text{-}min}$ is said oxygen concentration as a fractional weight of the minerals in said formation;
$k_{O\text{-}fl}$ is said oxygen concentration as a fractional weight of the fluids in said formation;
$k_{o\text{-}om}$ is said oxygen concentration as a fractional weight of the organic matter in said formation;
$\phi$ is said porosity of said formation;
$\rho_{fl}$ is said density of the fluid of said formation;
$\rho_{min}$ is said density of the minerals of said formation;
$\rho_{om}$ is said density of the organic matter of said formation;
$V_{om}$ is said fractional volume of organic matter in said formation; and
$\rho_{sol}$ is said combined density of said organic matter and said minerals of said formation.

16. A method according to claim 14, wherein:
said total carbon content is determined for a plurality of depths along said borehole in said formation.

17. A method according to claim 14, further comprising:
(i) determining the carbon content of said minerals in said formation; and
(j) determining the organic carbon content of said formation by subtracting said mineral carbon content from said determined total carbon content.

18. A method according to claim 17, wherein:
said organic carbon content is determined for a plurality of depths along said borehole in said formation.

19. A method according to claim 17, further comprising:
(k) identifying source rocks from said organic carbon content.

20. A method according to claim 14, wherein:
said carbon/oxygen ratio is measured by a borehole spectroscopy tool sensitive to the inelastic gamma ray spectrum.

* * * * *